(12) United States Patent
Masi et al.

(10) Patent No.: US 6,900,155 B2
(45) Date of Patent: May 31, 2005

(54) TITANIUM CATALYSTS, PREPARATION AND USE IN CO- AND TER-POLYMERIZATION OF ALPHA-OLEFINS

(75) Inventors: Francesco Masi, Sant' Angelo Lodigiano-Lodi (IT); Roberto Santi, Novara (IT); Stefano Ramello, Novara (IT); Anna Sommazzi, Santa Margherita Ligure-Genova (IT); Roberto Provera, Vercelli (IT); Antonio Proto, Novara (IT)

(73) Assignee: Polimer Europa S.p.A., Brindisi (IT)

( * ) Notice: Subject to any disclaimer, the term of this patent is extended or adjusted under 35 U.S.C. 154(b) by 0 days.

(21) Appl. No.: 10/474,208

(22) PCT Filed: Mar. 20, 2002

(86) PCT No.: PCT/EP02/03184
§ 371 (c)(1),
(2), (4) Date: Mar. 16, 2004

(87) PCT Pub. No.: WO02/085917
PCT Pub. Date: Oct. 31, 2002

(65) Prior Publication Data
US 2004/0143127 A1 Jul. 22, 2004

(30) Foreign Application Priority Data
Apr. 24, 2001 (IT) ...................................... MI2001A0858

(51) Int. Cl.$^7$ ................................ C07F 7/28; C08F 4/16
(52) U.S. Cl. ........................ 502/170; 556/55; 502/103; 502/104; 526/154; 526/172

(58) Field of Search ............................ 556/55; 502/103, 502/104, 170; 526/154, 172

(56) References Cited

PUBLICATIONS

F. Dawans: "Polymerization of butadiene in the presence of perfluorocarboxyl metal halides: control of the stereoregularity and the molecular weight" Angew. Makromol. Chem., vol. 50, No. 1, pp. 169–181, 1976.

S.R. Rafikov et al.: "Effect of the chemical nature of the substituent in titanium tetrachlorid derivatives on the Ziegler polymerization of butadiene" Bulletin of the Academy of Sciences of the USSR, Division of Chemical Science, vol. 24, No. 7, p. 1501, Jul. 1975.

Chemical Abstracts, vol. 104, No. 2 Jan. 13, 1986 abstract No. 6207, XP02181173, abstract only.

Chemical Abstracts, vol. 101, No. 10 Sep. 03, 1984 abstract No. 82965, XP002181174, abstract only.

*Primary Examiner*—Caixia Lu
(74) *Attorney, Agent, or Firm*—Oblon, Spivak, McClelland, Maier & Neustadt, P.C.

(57) ABSTRACT

Titanium complex having general formula (I) $(RCOO)_n TiX_p$ wherein R is a monofunctional hydrocarbyl radical having from 1 to 20 carbon atoms and a number of halogen atoms, selected from fluorine, chlorine and bromine, preferably chlorine, ranging from 1 to 6; X is chlorine, bromine or a beta-dicarbonyl group such as acetylacetone (AcAc), formylacetone, benzoylacetone, dibenzoylmethane; p+n=2, 3, 4, preferably p+n=3; n is greater than or equal to 1. The preparation of the above complex and its use in the co- and ter-polymerization of α-olefins, are also described.

24 Claims, No Drawings

TITANIUM CATALYSTS, PREPARATION AND USE IN CO- AND TER-POLYMERIZATION OF ALPHA-OLEFINS

BACKGROUND OF THE INVENTION

1. Field of the Invention

The present invention relates to a homogeneous catalyst based on titanium, its preparation and its use in the copolymerization of α-olefins and in the preparation of terpolymers of α-olefins with non-conjugated dienes.

The present invention also relates to a catalytic system comprising a titanium complex, a reducing/chlorinating agent based on a chlorinated aluminum alkyl and a cocatalyst based on aluminum trialkyl.

Finally the present invention relates to a process for the co- and ter-polymerization of α-olefins with non-conjugated dienes in the presence of said catalytic system.

2. Description of the Related Art

Ethylene-propylene (EPR) copolymers and the corresponding terpolymers with non-conjugated dienes (EPDM) are important elastomers and are industrially produced with catalysts based on vanadium such as $VCl_4$, $VOCl_3$, and $V(AcAc)_3$ which are soluble in many hydrocarbon solvents. Although these catalysts produce a highly random ethylene-propylene copolymer ($r_E \times r_P < 1$), their activities are greatly influenced by the temperature. This phenomenon is drastic and prevents their use at high temperatures. Furthermore, as is well known, the residues of these catalytic systems are toxic and tend to give the resulting polymers undesired colouring.

In this respect, heterogeneous titanium-based catalysts have been widely studied for the polymerization of ethylene or propylene, together with the methods for the preparation of these catalysts. Co-crystallized titanium (III) compounds have been prepared ($TiCl_3 \times 1/3\ AlCl_3$) for the reduction of $TiCl_4$ either with metallic aluminum or with organometallic derivatives of aluminum. $TiCl_3$ without $AlCl_3$ has also been prepared for the reduction of $TiCl_4$, with hydrogen, at temperatures of 800° C. Titanium catalysts supported on $MgCl_2$ or $SiO_2$ have also been prepared. The above catalysts based on $TiCl_3$ have an extremely high activity for the homopolymerization of ethylene and propylene but show a low activity compared with vanadium for the random copolymerization of these olefins. Heterogeneous titanium catalysts are therefore capable of copolymerizing ethylene with α-olefins such as propylene but only with low activities. The copolymers obtained, moreover, have partially isotactic propylene sequences with product values of the relative reactivities $r_E \times r_P > 5$; this result is reflected in block-type polymers, with crystalline domains, also due to long ethylene sequences and consequently not of the elastomeric type. These catalysts are also inactive towards the entrance of a possible diene termonomer.

SUMMARY

A new group of titanium-based catalysts, soluble in hydrocarbon solvents, has now been found, which, in the random co- and ter-polymerization of α-olefins, have higher catalytic activities than those observed with catalysts based on vanadium. With respect to other titanium-based catalysts, the catalytic systems of the present invention allow the production of highly random co- and ter-polymers and are active towards the entrance of a possible diene termonomer.

DETAILED DESCRIPTION OF THE INVENTION

A first object of the present invention therefore relates to a titanium complex having general formula (I)

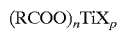  (I)

wherein R is a monofunctional hydrocarbyl radical having from 1 to 20 carbon atoms and a number of halogen atoms, selected from fluorine, chlorine and bromine, preferably chlorine, ranging from 1 to 6; X is selected from chlorine, bromine, a beta-dicarbonyl group; or 2 X=O;

p+n=2, 3, 4, preferably p+n=3;
n is greater than or equal to 1.

Typical examples of beta-dicarbonyl compounds are acetylacetone, formyl-acetone, benzoylacetone, dibenzoylmethane.

The carboxylic groups R—COO in formula (I) are selected from:

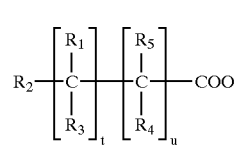  (1)

wherein $R_1$, $R_2$, $R_3$, $R_4$ and $R_5$, the same or different, are selected from H, F, Cl, Br, a mono functional hydrocarbyl radical optionally having at least one of its hydrogen atoms substituted with a halogen selected from chlorine, bromine, fluorine, preferably chlorine; with the proviso that at least one of the residues from $R_1$ to $R_5$ is selected from fluorine, chlorine or bromine, preferably chlorine, or a monofunctional hydrocarbyl group containing a halogen selected from fluorine, chlorine or bromine, preferably chlorine; t and u independently vary from 0 to 10.

Non-limiting examples of these derivatives are represented by:

$CCl_3COO$, $CCl_3CH_2COO$, $CCl_3(CH_2)_2COO$, $CHCl_2COO$, $CH_3CCl_2COO$, $C_6H_5Cl_2CH_2COO$, $(C_6H_5)_2CClCOO$, $CH_3CH_2CCl_2COO$, $C_6H_5(CH_2)_3CHClCOO$, $ClC_6H_4CHClCOO$, $ClC_6H_4CH_2COO$, 2-cyclopropyl-2,2-dichloro-acetic acid.

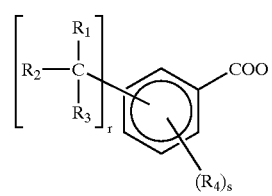  (2)

wherein:

$R_1$, $R_2$, $R_3$, $R_4$ have the same meaning defined above, with the proviso that at least one of the residues from $R_1$ to $R_4$ is selected from fluorine, chlorine or bromine, preferably chlorine, or a monofunctional hydrocarbyl group containing a halogen selected from fluorine, chlorine or bromine, preferably chlorine;

r and s independently vary from 0 to 5, with the constraint that r+s is from 1 to 5.

Non-limiting examples of these derivatives are represented by: $Cl_3CC_6H_4COO$, $ClCH_2C_6H_4COO$, $ClCH_2C_6H_2Cl_2COO$, $C_6Cl_5COO$.

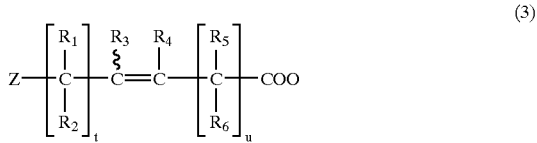

(3)

wherein:
$R_1$, $R_2$, $R_3$, $R_4$ have the same meaning defined above, Z, $R_5$, $R_6$ have the same meaning as the other substituents, with the proviso that at least one of the residues Z and $R_1$–$R_6$ is selected from fluorine, chlorine or bromine, preferably chlorine, or a monofunctional hydrocarbyl group containing a halogen selected from fluorine, chlorine or bromine, preferably chlorine; t and u independently vary from 0 to 10, preferably from 0 to 2.

Non-limiting examples of these derivatives are represented by:

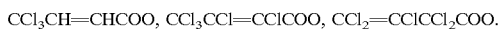

4) R—COO wherein R is a monofunctional hydrocarbyl radical selected from cycloalkyl, polycycloalkyl, cycloalkenyl, polycycloalkenyl having from 3 to 20 C atoms, substituted with at least a fluorine, chlorine or bromine, preferably at least one chlorine, or with hydrocarbyl groups containing at least a fluorine, chlorine or bromine, preferably chlorine.

Non-limiting examples of these derivatives are represented by:
2-chloro-cyclohexane-carboxylic acid, 2,2-dichlorocyclopropane-carboxylic acid, 2,2,3,3-tetrachlorocyclopropane-carboxylic acid, perchloro-cyclohexane-carboxylic acid, cyclo hex-2-ene-2-trichloromethyl-carboxylic acid.

Two processes for the preparation of the complexes having general formula (I) are objects of the present invention.

The first process comprises the following steps:
(a) treatment of a thallium salt having the general formula RCOOTl, wherein R has the meaning defined above, with a titanium compound having the general formula $TiY_nX_s$, wherein (n+s=2,3,4); s≧1; X is selected from chlorine, bromine, iodine, preferably chlorine; Y, the same as or different from X, is a group of an anionic nature bound to Ti as anion in an ionic couple or with a covalent bond of the "σ" type; said treatment being carried out in a hydrocarbyl solvent or in a chlorinated solvent, preferably heptane or toluene;
(b) separation, preferably filtration, of the thallium halide formed in step (a);
(c) isolation of the titanium compound having general formula (I).

Typical but non-limiting examples of $TiY_nX_s$, compounds are titanium halides, such as $TiCl_4$, $TiCl_3$, $TiCl_2(AcAc)_2$.

In the preferred embodiment, step (c) is carried out by evaporation of the solvent or precipitation of the complex following the addition of a suitable precipitant, usually a hydrocarbon solvent, preferably pentane.

Step (a) is preferably effected at a temperature ranging from 0 to 50° C., even more preferably from 15 to 30° C. At these temperatures, the duration of step (a) ranges indicatively from 30 minutes to 6 hours. Reaction times ranging from 1 to 4 hours are usually sufficient.

The second process comprises:
(a') The direct reaction between a titanium compound having the general formula $TiY_nX_s$ with one or more carboxylic acids having the general formula RCOOH in an aliphatic or aromatic hydrocarbon solvent or in a chlorinated solvent, preferably heptane or toluene, until the stoichiometric development of hydrochloric acid.
(b') Isolation of the titanium complex having general formula (I) formed in step (a').

In the preferred embodiment, step (b') is carried out by evaporation of the solvent or precipitation of the complex following the addition of a suitable precipitant, usually a hydrocarbon solvent, preferably pentane. Step (a') is preferably effected at a temperature ranging from 0 to 200° C., even more preferably from 15 to 120° C. At these temperatures, the duration of step (a') ranges indicatively from 30 minutes to 48 hours. Reaction times ranging from 1 to 16 hours are usually sufficient.

Typical but non-limiting examples of these syntheses are provided in the experimental part, which describes, among other things, the preparation of $Ti(CCl_3COO)_3$ by the reaction of $TiCl_3$ and $CCl_3COOH$ in a molar ratio of 1/3, $Ti(CCl_3COO)_2(AcAc)_2$ by the reaction between $TiCl_2(AcAc)_2$ and $Tl(CCl_3COO)$ in a molar ratio of 1/2, $Ti(CCl_3CH_2CH_2COO)_3$ by the reaction between $TiCl_3$ and $CCl_3CH_2CH_2COOTl$ in a ratio of 1/3, $Ti(CCl_3CH_2CH_2COO)_3$ by the reaction between $TiCl_3$ and $CCl_3CH_2CH_2COOH$ in a ratio of 1/3.

A further object of the present invention relates to a catalytic system for the co- and ter-polymerization of α-olefins comprising:
(a) a titanium complex having general formula (I),
(b) a reducing/chlorinating agent based on aluminum selected from those having general formula (II) $AlR_nX_{3-n}$ (with n=1 or 2) or (III) $Al_2R_nX_{6-n}$ (n=1–5) wherein R is a $C_1$–$C_{20}$ alkyl group, X is chlorine or bromine, preferably chlorine;
(c) an organo-aluminum having general formula (IV) $AlR_3$ wherein R is a $C_1$–$C_{20}$ alkyl group.

Typical examples of compounds having general formula (II) are $AlEt_2Cl$ (diethylchloroaluminum), $AlMe_2Cl$ (dimethylaluminumchloride), $AlEtCl_2$ (ethylaluminumdichloride), $Al(i-Bu)_2Cl$ (diisobutylaluminumchloride); typical examples of compounds having general formula (III) are $Al_2Et_3Cl_3$ (ethylaluminumsesquichloride), $Al_2Me_3Cl_3$ (methylaluminumses-quichloride).

The molar ratio between reducing/chlorinating agent having general formula (II) or (III) and the titanium complex having general formula (I) ranges from 1/1 to 20/1, preferably from 1.5/1 to 15/1, more preferably from 3/1 to 10/1.

Typical examples of compounds having general formula (IV) are $AlMe_3$ (trimethylaluminum), $AlEt_3$ (triethylaluminum), $Al(i-Bu)_3$ (triisobutylaluminum), $Al(n-oct)_3$ (trioctylaluminum). The molar ratio between said organo-aluminum having general formula (IV) and the titanium complex having general formula (I) ranges from 1/1 to 500/1, preferably from 3/1 to 100/1, more preferably from 10/1 to 50/1.

Typical but non-limiting examples of the preparation of the above catalytic system, useful for the copolymerization of α-olefins and terpolymerization of α-olefins with non-conjugated dienes, are the following:
A) contact of the reducing/chlorinating agent (b) with the titanium complex (a) dissolved in an aliphatic or aromatic hydrocarbon solvent, in the absence of the mixture of olefins to be polymerized and the aluminum trialkyl for a time ranging from 1 minute to 30 minutes, preferably from 5 to 20 minutes, at a temperature ranging from 0° C. to 50° C., preferably from 15° C. to 40° C. The catalytic precursor thus obtained is then fed to the mixture of olefins to be co- or ter-polymerized containing the aluminum trialkyl (c).

B) contact of the reducing/chlorinating agent with the titanium complex (a) dissolved in an aliphatic or aromatic hydrocarbon solvent containing the aluminum trialkyl (c), in the absence of the mixture of olefins to be polymerized, for a time ranging from 1 minute to 30 minutes, preferably from 5 to 20 minutes, at a temperature ranging from 0° C. to 50° C., preferably from 15° C. to 40° C.

C) contact of the aluminum trialkyl (c) with the titanium complex (a) dissolved in an aliphatic or aromatic hydrocarbon solvent in the absence of the chlorinating and/or reducing agent. The contact takes place separately in the absence of the mixture of olefins to be polymerized containing the reducing/chlorinating agent for a time ranging from 1 minute to 30 minutes, preferably from 5 to 20 minutes, at a temperature ranging from 0° C. to 50° C., preferably from 15° C. to 40° C. The catalytic precursor thus obtained is fed to the mixture of olefins to be polymerized containing the reducing/chlorinating agent (b).

D) contact in the polymerization reactor in the presence of the mixture of monomers. In this case, the three reagents aluminum trialkyl (c), chlorinating/reducing agent (b) having general formula (II) or (III) and titanium complex (a) can be added afterwards separately, in the order described, to the reactor containing the monomers to be polymerized.

The catalytic system is preferably prepared according to procedure (A).

The catalytic systems described above can be used in the copolymerization of α-olefins, preferably in the copolymerization of ethylene with propylene and possible higher α-olefins (for example 1-butene, 1-hexene, 1-octene) and in the terpolymerization of ethylene with propylene and non-conjugated dienes.

Particularly preferred are the copolymerization of ethylene-propylene to give elastomeric EPR copolymers and the terpolymerization of ethylene-propylene-non-conjugated diene to give EPDM rubbers.

In the case of the preparation of EPDM, the diene can be selected from:

alicyclic dienes with a linear chain such as 1,4-hexadiene and 1,6-octadiene;

acyclic dienes with a branched chain such as 5-methyl-1,4-hexadiene, 7-methyl-1,6-octadiene, 3,7-dimethyl-1,6-octadiene, 3,7-dimethyl-1,7-octadiene;

alicyclic dienes with a single ring such as 1,4-cyclohexadiene, 1,5-cyclo-octadiene;

dienes having condensed and bridged alicyclic rings such as methyltetrahydroindene, 5-ethylidene-2-norbornene (ENB), 5-propenyl-2-norbornene.

In the preferred embodiment the non-conjugated diene is selected from ENB and 7-methyl-1,6-octadiene.

The preparation processes of EPR copolymers and EPDM terpolymers are well known to experts in the field.

They are preferably carried out in liquid phase (solution or suspension) at low or medium pressure (15–50 atm.) and at temperatures ranging from −5 to 75° C.

In the preferred embodiment the temperature ranges from 25 to 60° C. and the pressure ranges from 6 to 35 atm.

The copolymers and terpolymers thus obtained have very high average molecular weights. If a molecular weight with a lower value is desired, it is possible to use hydrogen as molecular weight regulator.

Among the titanium complexes having general formula (I), those having general formula (I) wherein $R=CCl_3-$ $(-CH_2-)_n-$, wherein n is an integer ranging from 0 to 2, i.e. trichloroacetate (n=0), trichloropropionate (n=1), trichlorobutyrate (n=2), have proved to be particularly effective in the copolymerization reaction of α-olefins and in the preparation of EPDM copolymers.

The EPR and EPDM elastomeric copolymers obtained with the catalytic system of the present invention can contain propylene in a molar quantity ranging from 10 to 70% and non-conjugated diene in a molar quantity not greater than 15%. The weight average molecular weight of the polymers varies from 50,000 to 80,000.

Finally, it should be remembered that the elastomeric polymers which can be obtained with the catalytic system of the present invention do not show any undesired colouring effects of the polymer either in the transformation processes or in storage. Furthermore the catalytic residues are atoxic.

It should also be pointed out that it is possible to operate, according to the process of the present invention, with low quantities of aluminum chloroalkyls. In this way, the polymers obtained have a low chlorine content and can therefore be used in specialized applications, for example in the cable field.

The following examples are provided for a better understanding of the present invention.

EXAMPLES

The characterization by means of $^1$H-NMR spectroscopy was carried out on a Bruker MSL-200 spectrometer.

The characterization by means of FT-IR spectroscopy was carried out on an FT-IR Perkin-Elmer 1800 spectrometer with 4 cm$^{-1}$ resolution and 64 scans.

The titanium determination was effected on an inductively coupled plasma (ICP) spectrometer with atomic emission detection (AES) Perkin Elmer Plasma II.

The determination of the total Cl was effected using a Philips PW 1404/10 X-ray fluorescence(XRF) spectrometer with an Sc/Mo double anode tube.

The total chlorine was obtained by the sum of the inorganic chlorine (i.e. bound to titanium) and organic chlorine (i.e. chlorine bound to a hydrocarbyl residue).

The measurement was effected on alcohol solutions of the titanium complex diluted with Milliq water at 2% by weight of $HNO_3$ at a ratio of 1:100 for the determination of the titanium and 1:1 for that of the chlorine. The concentrations of titanium and chlorine were calculated on the basis of a calibration curve obtained with solutions with a known titer of the element to be determined (Ti or Cl) and having an identical composition to that of the samples (water, EtOH, $HNO_3$).

The determination of inorganic Cl was effected potentiometrically using a Titroprocessor 670 and an Ag electrode (cod. 6.0404.000) filled with a saturated solution of $KNO_3$ (both Metrohm). The alcohol solution of the sample was acidified with $H_2SO_4$ 3M and titrated with $AgNO_3$ 0.1 N.

The molecular weight measurement was effected by means of Gel-permeation chromatography (GPC). The analyses of the samples were carried out in 1,2,4-trichlorobenzene (stabilized with N,N'-m-phenylenedimaleimide) at 135° C. with a WATERS 150-CV chromatograph using a Waters differential refractometer as detector. The chromatographic separation was obtained with a set of μStyragel HT columns (Waters) with pore dimensions of $10^3$, $10^4$, $10^5$ and $10^6$ Å, establishing a flow-rate of the eluant of 1 ml/min. The results were obtained and processed by means of Maxima 820 software version 3.30 (Millipore). The calibration curve used for calculating the number (Mn) and weight (Mw) average molecular weight was obtained using standard polystyrene samples with molecular weights within the range of 6,500,000–2,000 and applying the Mark-Houwink equation valid for linear polyethylene and polypropylene; the molecular weight values were corrected in relation to the composition of the polymer using the Scholte equation.

The propylene content in the ethylene-propylene copolymers was determined on samples in film-form, using an FT-IR Perkin Elmer 1800 spectrometer with 4 cm$^{-1}$ resolution and 64 scans, by measuring the absorptions of the bands at 4390 and 4255 cm$^{-1}$, on the basis of the calibration curve set up with copolymers of a known composition.

Reagents and Solvents Used n-heptane (Aldrich): distilled on sodium; n-hexane (Aldrich): distilled on sodium; Dichloromethane (Aldrich): anhydrified on molecular sieves; Tetrahydrofuran (Aldrich): distilled on sodium; Toluene (Aldrich): distilled on sodium; Chloroform (Aldrich): anhydrified on molecular sieves; Ethyl ether (Aldrich); Molecular sieves (Aldrich); Acetylacetone (Aldrich): distilled at atmospheric pressure; titanium trichloride (Aldrich); titanium tetrachloride (Aldrich); Sodium sand in a 30% dispersion of toluene (Aldrich); TiO(acac)$_2$ (Aldrich); KOH (Aldrich), Benzyltrimethyl ammoniumchloride (Aldrich); Acrylonitrile (Aldrich); Tl$_2$CO$_3$ (Aldrich); Trichloroacetic acid (Aldrich); Dichloroacetic acid (Aldrich); Trifluoroacetic acid (Aldrich).

Example 1

Synthesis of Ti(acac)$_3$ (I)

6.11 g of acetylacetone (61.1 mmoles) dissolved in 50 ml of n-heptane are charged under argon into a 250 ml flask. 2.69 g of TiCl$_3$ (17.4 mmoles) are added. The mixture is left under stirring at reflux temperature for 16 hours. The solid is filtered, washed with hexane and dried at room temperature for 30 hours. 2.27 g (90% yield) of blue product are obtained.

Ti: 13.2% (13.91% theoretical value) Cl (ionic): <1% (0% theoretical value) Cl (total): <1% (0% theoretical value)

Example 2

Synthesis of TiCl$_2$(acac)$_2$ (II)
(Wilkie C. A., Lin G., Haworth D. T., *Inorg. Synth.*, 145, 19, 1979)

8.5 g of TiCl$_4$ (44.7 moles) dissolved in 50 ml of dichloromethane are charged under argon into a 250 ml flask. 11.0 g of acetylacetone (110 mmoles) are slowly added. The development of HCl is observed. The mixture is left under stirring at room temperature for 8 hours. The solvent is removed at the vacuum of the mechanical pump until a small volume remains, and hexane is then added. The solid is filtered, washed with hexane and dried at room temperature for 30 hours. 13.4 g (95% yield) of orange product are obtained.

Ti: 15.1% (15.12% theoretical value) Cl (ionic): 20.8% (22.43% theoretical value) Cl (total): 22% (22.43% theoretical value)

Example 3

Synthesis of Ti(OCOCCl$_3$)$_2$ (III)
Synthesis of TiCl$_4$(THF)$_2$ 5.0 g of TiCl$_4$ (26.4 moles) dissolved in 50 ml of CH$_2$Cl$_2$ are charged into a 250 ml flask. 7.62 g of THF (105.8 mmoles) are slowly added, and a yellow solution is obtained. 100 ml of n-hexane are then added, with the formation of a yellow precipitate which is filtered, washed with n-hexane (2×50 ml) and subsequently dried at the vacuum of the mechanical pump for 12 hours. 8.1 g (92% yield) of yellow product are obtained.

Synthesis of TiCl$_2$(THF)$_{2.2}$ (Calderazzo F. et al., *Z. Naturforsh.* 506, 51b, 1996)

0.9 g of sodium sand (37.5 mmoles) are added to a solution of 5.2 g of TiCl$_4$(THF)$_2$ (15.6 mmoles) in 100 ml of THF. The colour of the solution slowly turns from yellow to green and then to black. The suspension is kept under stirring for 48 hours and is then filtered. Upon the addition of 100 ml of n-hexane to the filtrate, the formation of a black precipitate is observed, which is recovered by filtration, washed with n-hexane (2×50 ml) and dried at the vacuum of the mechanical pump for 12 hours. 2.7 g (40% yield) of product are obtained in the form of a black solid.

Ti: 17.1% (17.25% theoretical value) Cl (ionic): 24.1% (25.55% theoretical value) Cl (total): 25.2% (25.55% theoretical value)

Synthesis of the Complex Ti(OCOCCl$_3$)$_2$ 6.65 g of CCl$_3$COOH (40.71 mmoles) dissolved in 50 ml of n-heptane are charged under argon into a 250 ml flask. 1.92 g of TiCl$_2$(THF)$_2$ (7.3 mmoles) are added. The mixture is left under stirring at reflux temperature for 6 hours. The solid is filtered, washed with hexane and dried at room temperature for 30 hours. 2.37 g (80% yield) of brown product are obtained.

Ti: 12.0% (12.83% theoretical value) Cl (ionic): 5.01% (0% theoretical value) Cl (total): 48.0% (57.12% theoretical value) IR (nujol): 1638 cm$^{-1}$ ($v_{asymm}$ CO$_2$); 1398 cm$^{-1}$ ($v_{symm}$ CO$_2$)

Example 4

Synthesis of Ti(OCOCCl$_3$)$_3$ (IV)

10.66 g of CCl$_3$COOH (65.25 mmoles) dissolved in 50 ml of n-heptane are charged under argon into a 250 ml flask. 3.13 g of TiCl$_3$ (20.30 mmoles) are added. The mixture is left under stirring at reflux temperature for 8 hours. The solid is filtered, washed with hexane and dried at room temperature for 30 hours. 9.66 g (89% yield) of brown product are obtained.

Ti: 8.70% (8.94% theoretical value) Cl (ionic): <1% (0% theoretical value) Cl (total): 57.9% (59.67% theoretical value) IR (nujol): 1609 cm$^{-1}$ ($v_{asymm}$ CO$_2$); 1404 cm$^{-1}$ ($v_{asymm}$ CO$_2$)

Example 5

Synthesis of TiCl(OCOCCl$_3$)$_2$ (V)

4.01 g of CCl$_3$COOH (24.55 mmoles) dissolved in 50 ml of n-heptane are charged under argon into a 250 ml flask. 1.89 g of TiCl$_3$ (12.26 mmoles) are added. The mixture is left under stirring at reflux temperature for 8 hours. The solid is filtered, washed with hexane and dried at room temperature for 30 hours. 4.0 g (80% yield) of brown product are obtained.

Ti: 11.6% (11.72% theoretical value) Cl (ionic): 8.21% (8.69% theoretical value) Cl (total): 51.87% (52.15% theoretical value) IR (nujol): 1607 cm$^{-1}$ ($v_{asymm}$ CO$_2$); 1403 cm$^{-1}$ ($v_{symm}$ CO$_2$)

Example 6

Synthesis of TiCl$_2$(OCOCCl$_3$) (VI)

2.79 g of CCl$_3$COOH (17.08 mmoles) dissolved in 50 ml of n-heptane are charged under argon into a 250 ml flask.

2.66 g of $TiCl_3$ (17.25 mmoles) are added. The mixture is left under stirring at reflux temperature for 8 hours. The solid is filtered, washed with hexane and dried at room temperature for 30 hours. 3.94 g (82% yield) of brown product are obtained.

Ti: 15% (17.01% theoretical value) Cl (ionic): 23% (25.23% theoretical value) Cl (total): 57% (63.08% theoretical value) IR (nujol): 1608 cm$^{-1}$ ($v_{asymm}$ $CO_2$); 1404 cm$^{-1}$ ($v_{symm}$ $CO_2$)

Example 7

Synthesis of TiO(acac)(OCOCCl$_3$) (VII)

8.41 g of $CCl_3COOH$ (51.5 mmoles) dissolved in 50 ml of n-heptane are charged under argon into a 250 ml flask. 3.01 g of $TiO(acac)_2$ (11.49 mmoles) are added. The mixture is left under stirring at reflux temperature for 8 hours. The solvent is removed at the vacuum of the mechanical pump. 50 ml of toluene are added to the solid mass thus obtained, having a rubbery consistency and orange-coloured. A solid is separated, which is filtered, washed with hexane and dried at room temperature for 30 hours. 1.5 g (40% yield) of yellow product are obtained.

Ti: 13.4% (14.7% theoretical value) Cl (total): 31% (32.71% theoretical value) IR (nujol): 1675 cm$^{-1}$ ($v_{asymm}$ $CO_2$); 1352 cm$^{-1}$ ($v_{asymm}$ $CO_2$)

Example 8

Synthesis of TiCl(OCOCH$_2$CH$_2$CCl$_3$)$_2$ (VIII)
Synthesis of 4,4,4-trichloro-butyro-nitrile (Bruson H. A. et al. *J. Am. Chem. Soc.* 601, 67, 1945)

242 ml of $CHCl_3$ (3.02 moles), 36 g of $[C_6H_5CH_2N(CH_3)_3]^+[Cl]^-$ (0.196 moles, BTMACl) and 11.0 g of KOH (0.196 moles) in 27 ml of water, are charged into a three-necked flask equipped with a mechanical stirrer, a drip funnel and double-branched fitting connected to a nitrogen line and equipped with a thermometer. After cooling to 05° C. by means of a cryostat, 300 ml of $CH_2$=CHCN (4.56 moles) are added in about three hours. The mixture is left under stirring at this temperature for 24 hours. The reaction mixture is washed three times with water. The aqueous phase is extracted with ethyl ether. The ether and chloroform phases are joined and concentrated. The mixture is distilled and the fraction which passes at 91–103° C. is collected (16 mmHg). The distillate obtained which solidifies in the flask weighs 91.0 g (17% yield).

$^1$H-NMR (CDCl$_3$, δ in ppm): 3.08 (2H, t), 2.85 (2H, t). IR (in nujol): 2260 cm$^{-1}$ ($v_{CB}$)
Synthesis of 4,4,4-trichloro-butyric acid 40.5 g of 4,4,4-trichloro-butyronitrile (0.236 moles) and 170 ml of concentrated HCl are charged into a 250 ml flask. The mixture is left under stirring at 60° C. for 6 hours. The solid acid precipitates and is filtered, washed with water and dried with the mechanical pump. 43.4 g (97% yield) of 4,4,4-trichloro-butyric acid are obtained. Melting point: 54.8° C. (reading 55° C.)

$^1$H-NMR (CDCl$_3$, δ in ppm): 10.82 (1H, s broad), 3.15 (2H, t), 2.92 (2H, t). IR (in nujol): 3260 cm$^{-1}$ ($v_{OH}$), 1720 cm$^{-1}$ ($v_{CO}$).
Synthesis of TiCl(OCOCH$_2$CH$_2$CCl$_3$)$_2$ 18.62 g of $CCl_3CH_2CH_2COOH$ (97.5 mmoles) dissolved in 50 ml of toluene are charged under argon into a 250 ml flask. 5.0 g of $TiCl_3$ (32.4 mmoles) are added. The mixture is left under stirring at reflux temperature for 8 hours. The solvent is removed at the vacuum of the mechanical pump. The solid is recovered with 50 ml of n-hexane and left under stirring for 2 hours; it is then filtered, washed with hexane and dried at room temperature for 30 hours. 12.9 g (86% yield) of green product are obtained.

Ti: 8.7% (10.3% theoretical value) Cl (ionic): 9.3% (7.6% theoretical value) Cl (total): 51% (53.50% theoretical value) IR (nujol): 1549 cm$^{-1}$ ($v_{asymm}$ $CO_2$); 1430 cm$^{-1}$ ($v_{symm}$ $CO_2$)

Example 9

Synthesis of Ti(OCOCH$_2$CH$_2$CCl$_3$)$_3$ (IX)

31.0 g of $CCl_3CH_2CH_2COOH$ (162.3 mmoles) dissolved in 50 ml of toluene are charged under argon into a 250 ml flask. 5.0 g of $TiCl_3$ (32.4 mmoles) are added. The mixture is left under stirring at reflux temperature for 16 hours. A blue solution is obtained. The solvent is removed at the vacuum of the mechanical pump. The solid is recovered with 50 ml of n-hexane and left under stirring for 2 hours; it is then filtered, washed with hexane and dried at room temperature for 30 hours. 17.8 g (89% yield) of green product are obtained.

Ti: 8.7% (7.73% theoretical value) Cl (ionic): 2.5% (0% theoretical value) Cl (total): 55% (51.57% theoretical value) IR (nujol): 1550 cm$^{-1}$ ($v_{asymm}$ $CO_2$); 1430 cm$^{-1}$ ($v_{symm}$ $CO_2$)

Example 10

Synthesis of TiO(acac)$_2$(OCOCCl$_3$)$_2$ (X)
Synthesis of Thallium Trichloroacetate—Tl(OCOCCl$_3$)

7.7 g of trichloroacetic acid (47.15 mmoles) are added to a suspension of 10.4 g of $Tl_2CO_3$ (22.22 mmoles) in 100 ml of methanol, maintained under stirring. The mixture is left under stirring for 4 hours at room temperature. The solution is then filtered and the filtrate is evaporated at 20° C. and 20 mmHg. The solid obtained is washed with ethyl ether (2×50 ml) and dried at 10$^{-3}$ mmHg. 14.1 g (91% yield) of thallium salt are obtained in the form of a white solid.
Synthesis of Ti(acac$_2$) (OCOCCl$_3$)$_2$ 4.01 g of TlOCOCCl$_3$ (12.65 mmoles) are added to a solution obtained by dissolving 1.48 g of $TiCl_2(acac)_2$ (4.68 mmoles) in 50 ml of toluene. The reaction is carried out for 36 hours at room temperature. The TlCl in suspension is filtered and the solvent is evaporated. 50 ml of n-hexane are added to the product obtained, the mixture is left under stirring for 4 hours, is then filtered, washed with hexane and dried at room temperature for 30 hours. 2.5 g (94% yield) of orange product are obtained.

Ti: 8.2% (8.39% theoretical value) Cl (total): 37.9% (37.32% theoretical value) IR (nujol): 1722, 1707 cm$^{-1}$ ($v_{asymm}$ $CO_2$); 1307 cm$^{-1}$ ($v_{asymm}$ $CO_2$) DCI-MS negative ions: m/z 570 [M]$^-$ DCI-MS positive ions: m/z 408 [M—(OCOCCl$_3$)]$^+$ $^1$H-NMR (CDCl$_3$, δ in ppm): 5.98 (1H, s), 2.17 (6H, s).

Example 11

Synthesis of Ti(acac)$_2$(OCOCF$_3$)$_2$ (XI)
Synthesis of Thallium Trifluoroacetate—Tl(OCOCF$_3$)

3.5 g of trifluoroacetic acid (30.7 mmoles) are added to a suspension of 6.3 g of $Tl_2CO_3$ (13.43 mmoles) in 100 ml of methanol, maintained under stirring. The mixture is left under stirring for 4 hours at room temperature. The solution is then filtered and the filtrate is evaporated at 20° C. and 20 mmHg. The solid obtained is washed with ethyl ether (2×50 ml) and dried at 10$^{-3}$ mmHg. 8.1 g (95% yield) of thallium salt are obtained in the form of a white solid.

Synthesis of Ti(acac$_2$) (OCOCF$_3$)$_2$ 6.12 g of TlOCOCF$_3$ (19.3 mmoles) are added to a solution obtained by dissolving 2.70 g of TiCl$_2$(acac)$_2$ (8.54 mmoles) in 50 ml of toluene. The reaction is carried out for 36 hours at room temperature. The TlCl in suspension is filtered and the solvent is evaporated. 50 ml of n-hexane are added to the product obtained, the mixture is left under stirring for 4 hours, is then filtered, washed with hexane and dried at room temperature for 30 hours. 3.75 g (93% yield) of yellow product are obtained.

Ti: 10.2% (10.1% theoretical value) Cl (ionic): <0.3% (0% theoretical value) IR (CH$_2$Cl$_2$ solution): 1713 cm$^{-1}$, ($v_{asymm}$ CO$_2$); 1466 cm$^{-1}$ ($v_{symm}$ CO$_2$)

Example 12

Synthesis of Ti(acac)$_2$(OCOCECl$_2$)$_2$ (XII)

Synthesis of Thallium Dichloroacetate—Tl(OCOCHCl$_2$)

7.2 g of dichloroacetic acid (56.25 mmoles) are added to a suspension of 11.6 g of Tl$_2$CO$_3$ (24.73 mmoles) in 100 ml of methanol, maintained under stirring. The mixture is left under stirring for 4 hours at room temperature. The solution is then filtered and the filtrate is evaporated at 20° C. and 20 mmHg. The solid obtained is washed with ethyl ether (2×50 ml) and dried at 10$^{-3}$ mmHg. 15.1 g (92% yield) of thallium salt are obtained in the form of a white solid.

Synthesis of Ti(acac$_2$) (OCOCHCl$_2$)$_2$ 5.11 g of TlOCOCHCl$_2$ (15.4 mmoles) are added to a solution obtained by dissolving 2.3 g of TiCl$_2$(acac)$_2$ (7.3 mmoles) in 50 ml of toluene. The reaction is carried out for 36 hours at room temperature. The TlCl in suspension is filtered and the solvent is evaporated. 50 ml of n-hexane are added to the product obtained, the mixture is left under stirring for 4 hours, is then filtered, washed with hexane and dried at room temperature for 30 hours. 3.33 g (90% yield) of orange product are obtained.

Ti: 9.1% (9.52% theoretical value) Cl (ionic): <1% Cl (total): 28.25% IR (CH$_2$Cl$_2$ solution): 1710 cm$^{-1}$, ($v_{asymm}$ CO$_2$); 1333 cm$^{-1}$ ($v_{symm}$ CO$_2$) DCI-MS negative ions: m/z 502 [M]$^-$ DCI-MS positive ions: m/z 374 [M—(OCOCHCl$_2$)]$^+$

Example 13

Synthesis of Titanium tris-(4,4,4-trichloro-but-2-enoate) (CCl$_3$CH=CHCOO)$_3$Ti (XIII)

1) Synthesis of 4,4,4-tricholoro-but-2-enoic acid

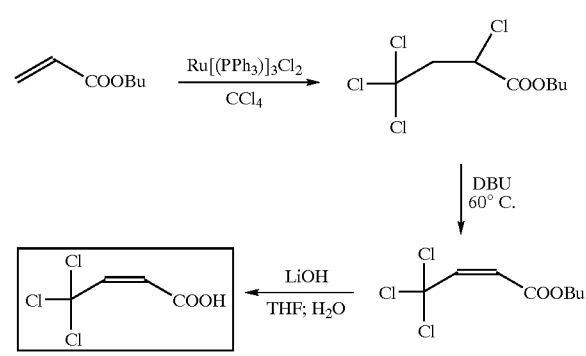

a) Synthesis of tris(triphenylphosphine) Ruthenium Dichloride

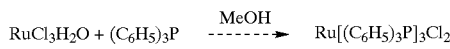

0.5 g of RuCl$_3$.H$_2$O are dissolved under argon in 150 ml of anhydrous methanol and the solution is refluxed for 5 minutes. It is brought to room temperature and 2.3 g of triphenylphosphine are added. The mixture is brought back to reflux temperature for three hours. It is cooled to room temperature, filtered and the solid obtained is dried at 25° C. and 10$^{-3}$ mmHg.

b) Synthesis of Butyl 4,4,4,2-tetrachlorobutenoate

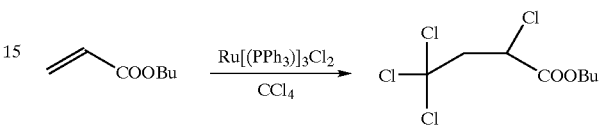

12 g of butylacrylate (94 mmoles), 200 mg of RuCl$_2$[PPh$_3$]$_3$ and 28 ml of carbon tetrachloride are charged under argon into a 500 ml flask. The temperature is brought to 90° C. for about 4 hours. Upon GC control, it can be observed that the reaction is complete. The mixture is cooled, petroleum ether is added and the triphenylphosphine which precipitates is filtered. Upon evaporation of the solvent, 13 g of raw residue are obtained which is used directly in the subsequent passage.

c) Synthesis of Butyl 4,4,4-trichloro-but-2-enoate

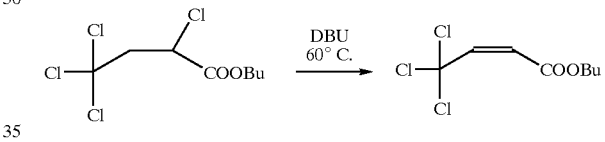

6 g of butyl 4,4,4,2-tetrachloride butanoate (22.4 mmoles) in 20 ml of anhydrous toluene are charged under inert gas into a 250 ml flask and 5 ml of 1,8-diazabicylco[5.4.0]undecan-7-ene (DBU) are added with exothermy. The mixture is brought to 60° C. for 3 hours. Upon GC control, it is observed that the reaction is complete; the mixture is cooled, water is added, the mixture is extracted with ethyl ether and anhydrified on Na$_2$SO$_4$. The residue obtained after evaporation of the solvent and purification by means of silica gel chromatography (eluant: hexane/ethyl acetate=9/1) weighs 4 g (76% yield).

d) Synthesis of 4,4,4-trichloro-but-2-enoic acid

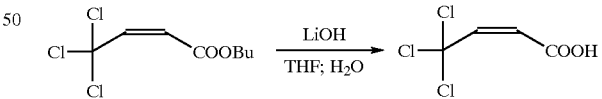

17.82 g of LiOH in 20 ml of water are added to a solution containing 3 g of butyl 4,4,4-trichloro-but-2-enoate (0.0128 moles) in 300 ml of THF. The mixture is stirred for 1 hour at room temperature. The mixture is then brought to neutral pH by the addition of HCl 1N, is extracted with ethyl acetate and anhydrified on Na$_2$SO$_4$. The solid obtained after evaporation of the solvent at reduced pressure and washing with petroleum ether weighs 2.1 g (87% yield).

e) Synthesis of Thallium 4,4,4-trichloro-but-2-enoate (CCl$_3$CH=CHCOO) Tl 1.56 g of 4,4,4-trichloro-but-2-enoic acid (8.4 mmoles) are added to a suspension of 1.94 g of Tl$_2$CO$_3$ (4.2 mmoles) in 80 ml of methanol, maintained under stirring. The mixture is left under stirring for 4 hours at room temperature. The solution is then filtered and evaporated at 15° C. and 20 mmHg. The solid obtained is washed with ethyl ether (10×50 ml) and dried at $10^{-3}$ mmHg. 3.0 g of thallium salt are obtained in the form of a white solid (91.2% yield).

f) Synthesis of Titanium tris-(4,4,4-trichloro-but-2-enoate ($CCl_3CH=CHCOO$)Ti 0.79 g (2.15 mmoles) of $TiCl_3.(THF)_3$ dissolved in 60 ml of anhydrous THF are charged under argon into a 150 ml test-tube. 3 g of $CCl_3CH=CHCOOTl$ (6.54 mmoles) are slowly added. The solution changes colour. It is left under stirring for about 4 hours. The solution is filtered, evaporated and the resulting solid is dried at $10^{-3}$ mmHg for 24 hours. 1.40 g of complex are obtained (95% yield).

Ti: 7.8%; Cl: 52.1%

Example 14

Synthesis of Titanium tris-(2,4-dichloro-phenylacetate) $(2,4—Cl_2—C_6H_3—CH_2—COO)_3Ti$ (XIV)

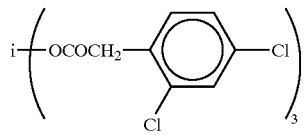

A solution of 2,4-dichlorohpenylacetic acid (Acros) in toluene (11.3 g, 55 mmoles in 150 ml of solvent) is added, by siphoning, to a suspension of 2.8 g (18.2 mmoles) of $TiCl_3$ in 100 ml of toluene, and 0.3 ml of diisopropylethylamine are subsequently added. The mixture is heated to reflux temperature for 5 hours. It is cooled, the volume is reduced by evaporation under vacuum and is then filtered. Upon evaporation of the filtrate, 12 g of a shiny solid are obtained (100% yield).

Ti: 7.25%; Cl: 33%

Example 15

Synthesis of titanium tris-[1-(α-chloromethyl)-benzoate] $(ClCH_2C_6H_4COO)_3Ti$ (XV)

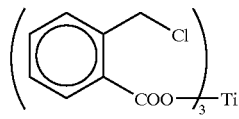

Synthesis of thallium [1-(α-chloro-methyl)-benzoate]

1.43 g (8.4 mmoles) of 1-(α-chloro-methyl)-benzoic acid are added to a suspension of 1.94 g of $Tl_2CO_3$ (4.2 mmoles) in 80 ml of methanol, maintained under stirring. The mixture is left under stirring for 4 hours at room temperature. The solution is then filtered and evaporated at 15° C. and 20 mmHg. The solid obtained is washed with ethyl ether (10×50 ml) and dried at $10^{-3}$ mmHg. 3.0 g of thallium salt are obtained in the form of a white solid (97% yield).

Synthesis of Titanium [1-(α-chloro-methyl)-benzoate]

0.79 g (2.15 mmoles) of $TiCl_3.(THF)_3$ dissolved in 60 ml of anhydrous THF are charged under argon into a 150 ml test-tube. 2.44 g of thallium [1-(α-chloro-methyl)-benzoate] (6.54 mmoles) are slowly added. The solution is left under stirring for about 12 hours. It is then filtered. The filtrate is evaporated and the resulting solid is dried at $10^{-3}$ mmHg for 24 hours. 1.13 g of complex are obtained (95% yield).

Ti: 8.6%; Cl: 19%

Example 16

Synthesis of Titanium tris-[2-chloro-cyclohexanecarboxylate) (XVI)

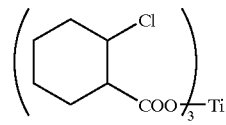

Synthesis of Thallium 2-chloro-cyclohexanecarboxylate 1.36 g (8.4 mmoles) of 2-chloro-cyclohexanecarboxylic acid are added to a suspension of 1.94 g of $Tl_2CO_3$ (4.2 mmoles) in 80 ml of methanol, maintained under stirring. The mixture is left under stirring for 8 hours at room temperature. The solution is filtered and evaporated at 15° C. and 20 mmHg. The solid obtained is washed with ethyl ether (10×50 ml) and dried at $10^{-3}$ mmHg. 3.0 g of thallium salt are obtained in the form of a white solid (97% yield).

Synthesis of titanium tris-(2-chloro-cyclohexane-carboxylate)

0.79 g (2.15 mmoles) of $TiCl_3.(THF)_3$ dissolved in 61 ml of anhydrous THF are charged under argon into a 150 ml test-tube. 2.39 g of thallium 2-chloro-cyclohexane-carboxylate (6.54 mmoles) are slowly added. The solution is left under stirring for about 12 hours. It is then filtered. The filtrate is evaporated and the resulting solid is dried at $10^{-3}$ mmHg for 24 hours. 1.13 g of complex are obtained (98% yield).

Ti: 9%; Cl: 20%

Example 17

Synthesis of Titanium tris-(2-phenyl-3,3'-dichloro-butanoate) $Ti[OCOCH(C_6H_5)CCl_2CH_3]_3$ (XVII)

A solution of 12.8 g (55 mmoles) of 2-phenyl-3,3'-dichloro-butanoic acid in 150 ml of toluene is added, by siphoning, to a suspension of 2.8 g (18.2 mmoles) of $TiCl_3$ in 100 ml of toluene, and 0.3 ml of diisopropylethylamine are subsequently added. The mixture is heated to reflux temperature for 5 hours. It is cooled, the volume is reduced by evaporation under vacuum and is then filtered. Upon evaporation of the filtrate, 11 g of a shiny solid are obtained (81% yield).

Ti: 6.4%; Cl: 29%

Example 18

Synthesis of Titanium tris-(2,2'-dichloro-3-phenyl-propanoate) $Ti[OCOCCl_2C(C_6H_5)]3$ (XVIII)

A solution of 12.0 g (55 mmoles) of 2,2'-dichloro-3-phenyl-propanoic acid in 150 ml of toluene is added, by siphoning, to a suspension of 2.8 g (18.2 mmoles) of $TiCl_3$ in 100 ml of toluene, and 0.3 ml of diisopropylethylamine are subsequently added. The mixture is heated to reflux temperature for 8 hours. It is cooled, concentrated and filtered. Upon evaporation of the filtrate, 12 g of a solid product are obtained (94% yield).

Ti: 6.82%; Cl: 30.3%

Examples 19–28

Ethylene-Propylene Copolymerization in Solution

A vacuum-nitrogen is created for at least three times at 90° C. and for a total duration of about 2 hours, in a Bu-chi autoclave with a 2 L steel reactor equipped with a burette for the introduction of the catalyst, a propeller stirrer, thermo-resistance and heating jacket connected to a thermostat for the temperature control. Before each test, a flushing of the reactor is effected by maintaining under stirring at 90° C. a solution containing 500 ml of anhydrous heptane and 5 ml of Al(i-Bu)$_3$ for about 2 hours. The contents of the reactor are discharged through a valve situated at the bottom under slight nitrogen pressure and a solution containing 1 l of heptane and Al(i-Bu)$_3$ in such a quantity as to respect an Al/Ti ratio=50, is charged into the autoclave. The autoclave is pressurized by introducing, in order, 200 g of propylene (4.9 atm) and 7 g of ethylene (1 atm) and the whole mixture is thermostat-regulated at 30° C. At this point, a solution of the Ti complex obtained by dissolving 0.042 mmoles in 10 ml of toluene with pre-contact for 30 minutes with aluminum sesquichloride (EASC) in such a quantity as to respect the desired Al/Ti ratio, is introduced through the burette situated at the head of the autoclave, using a slight over-pressure of nitrogen. Once the catalyst has been charged, the reaction is left for 1 hour, the system being maintained at constant pressure by means of a stream of ethylene. At the end, the contents of the reactor are discharged under pressure by means of the valve situated on the bottom and coagulated in about 3 l of ethanol. The polymer is separated by means of filtration, washed with acetone and anhydrified under vacuum at 40° C. for about 8 hours.

Examples 29–32

Ethylene-Propylene Copolymerization in Solution

The procedure is identical to that described for examples 19–28 with the only exception that a solution containing 700 ml of heptane and Al(i-Bu)$_3$ in such a quantity as to respect an Al/Ti ratio=50, is charged into the autoclave; the autoclave is then pressurized by introducing 190 g of propylene (6.7 atm) and the whole mixture is thermo-stat-regulated at 30° C.

Table 2 indicates the results of the relative experiment.

Examples 33–36

Ethylene-propylene-5-ethylidene-2-norbornene (ENB) Terpolymerization in Solution.

The procedure is identical to that described for examples 19–28 with the only exception that a solution containing 1 l of heptane, 10 ml of ENB (75 mmoles) and Al(i-Bu)$_3$ in such a quantity as to respect an Al/Ti ratio=50, is charged into the autoclave.

Table 3 indicates the results of the relative experiment.

Example 37

Ethylene-propylene-7-methyl-1,6-octadiene Terpolymerization in Solution

The procedure is identical to that described for examples 33–36 with the only exception that 7-methyl-1,6-octadiene is used instead of ENB.

Table 4 indicates the results of the relative experiment.

Examples 38–41

Ethylene-propylene copolymerization in liquid propylene.

A vacuum-nitrogen is created for at least three times at 90° C. and for a total duration of about 2 hours, in a Bu-chi autoclave with a 500 ml steel reactor equipped with a burette for the introduction of the catalyst, a propeller stirrer, thermo-resistance and heating jacket connected to a thermostat for the temperature control. Before each test, a flushing of the reactor is effected by maintaining under stirring at 90° C. a solution containing 250 ml of anhydrous heptane and 2 ml of Al(i-Bu)$_3$ for about 2 hours. The contents of the reactor are discharged through a valve situated at the bottom under slight nitrogen pressure and 120 g of liquid propylene are charged into the autoclave at 23° C. The reactor is then brought to the polymerization temperature of 40° C. and a quantity of Al(i-Bu)$_3$ which is such as to respect an Al/Ti ratio=50, is introduced; gaseous ethylene is then charged until the desired equilibrium pressure is reached (20–22 atm). At this point, a solution of the Ti complex obtained by dissolving 0.042 mmoles in 10 ml of toluene with pre-contact for 30 minutes with aluminum sesquichloride (EASC) in such a quantity as to respect a Al/Ti ratio=6, is introduced through the burette situated at the head of the autoclave, using a slight overpressure of nitrogen. Once the catalyst has been charged, the reaction is left for 1 hour, the system being maintained at constant pressure by means of a stream of ethylene. At the end, the polymerization is stopped by the rapid degassing of the residual monomers. The polymer is recovered after washing with ethyl alcohol and is dried at 40° C. for about 8 hours under vacuum.

Table 5 indicates the results of the relative experiment.

TABLE 1

CATALYTIC SYSTEMS BASED ON TITANIUM CLHOROCARBOXYLATES
COPOLYMERIZATION OF ETHYLENE AND PROPYLENE

| Example | Catalyst | Al/Ti mol/mol | Yield g | Activity $g_{pol}/g_{Ti}$ | $C_3$ % moles | $r_E x r_P$ | $M_w \times 10^{-3}$ | MWD |
|---|---|---|---|---|---|---|---|---|
| 19 Comp | Ti(AcAc)$_3$ (I) | 3 | 7.0 | 3500 | 26.3 | — | 459 | 51.3 |
| 20 Comp | Ti(AcAc)$_3$ (I) | 6 | 15.4 | 7600 | 31.1 | 1.10 | 674 | 13.5 |
| 21 Comp | Ti(AcAc)$_2$Cl$_2$ (II) | 3 | 19.2 | 9600 | 38.3 | 1.23 | 847 | 24.8 |
| 22 | Ti(OCOCCl$_3$)$_3$ (IV) | 3 | 10.1 | 5000 | 28.1 | 0.81 | 830 | 13.5 |
| 23 | Ti(OCOCCl$_3$)$_3$ (IV) | 6 | 26.0 | 12900 | 33.1 | 0.81 | 602 | 8.1 |
| 24 | TiCl(OCOCH$_2$CH$_2$CCl$_3$)$_2$(VIII) | 6 | 27.0 | 13400 | 33.1 | 0.87 | 77 | 2.4 |
| 25 | Ti(OCOCH$_2$CH$_2$CCl$_3$)$_3$ (IX) | 6 | 34.6 | 17200 | 31.9 | 0.75 | 148 | 3.1 |
| 26 | Ti(AcAc)$_2$(OCOCCl$_3$)$_2$ (X) | 6 | 17.0 | 8500 | 27.0 | — | 173 | 4.1 |
| 27 | Ti(OCOCH=CHCCl$_3$)$_3$ (XIII) | 6 | 7.0 | 3500 | 26.1 | — | 128 | 4.0 |
| 28 | Ti(OCOCH$_2$PhCl$_2$)$_3$ (XIV) | 6 | 8.5 | 4000 | 25.4 | — | 216 | 3.2 |

TABLE 2

CATALYTIC SYSTEMS BASED ON TITANIUM CHLOROCARBOXYLATES COPOLYMERIZATION OF ETHYLENE AND PROPYLENE

| Ex. | Catalyst | Al/Ti mol/mol | Yield g | Activity $g_{pol}/g_{Ti}$ | $C_3$ % moles | $r_E x r_P$ | $M_w \times 10^{-3}$ | MWD |
|---|---|---|---|---|---|---|---|---|
| 29C | $Ti(AcAc)_3$ (I) | 6 | 2.5 | 1250 | 55.5 | 1.27 | 459 | 27 |
| 30 | $Ti(OCOCCl_3)_3$ (IV) | 6 | 5.6 | 2800 | 62.6 | — | 431 | 13 |
| 31 | $TiCl(OCOCH_2CH_2CCl_3)_2$ (VIII) | 6 | 3.6 | 1800 | 70.7 | — | 534 | 10 |
| 32 | $Ti(OCOCH_2CH_2CCl_3)_3$ (IX) | 6 | 9.3 | 4600 | 66.4 | 0.46 | 185 | 4.8 |

TABLE 3

CATALYTIC SYSTEMS BASED ON TITANIUM CHLOROCARBOXYLATES ETHYLENE-PROPYLENE-ENB TERPOLYMERIZATION

| Ex. | Catalyst | Al/Ti m/m | Yield g | Activity $g_{pol}/g_{Ti}$ | $C_3$ % moles | ENB % moles | $r_E x r_P$ | $M_w \times 10^{-3}$ | MWD |
|---|---|---|---|---|---|---|---|---|---|
| 33C | $Ti(AcAc)_3$ (I) | 6 | 1.1 | 550 | 28.5 | 0.5 | 1.61 | 459 | 27.3 |
| 34 | $Ti(OCOCCl_3)_3$ (IV) | 3 | 1.4 | 700 | 32.7 | 1.2 | 0.91 | 130 | 3.6 |
| 35 | $TiCl(OCOCH_2CH_2CCl_3)_2$ (VIII) | 6 | 3.0 | 1500 | 40.8 | 1.4 | — | 261 | 2.7 |
| 36 | $Ti(OCOCH_2CH_2CCl_3)_3$ (IX) | 6 | 8.8 | 4400 | 27.2 | 1.1 | — | 186 | 3.4 |

TABLE 4

CATALYTIC SYSTEMS BASED ON TITANIUM CHLORO-CARBOXYLATES ETHYLENE-PROPYLENE-7-METHYL-1,6-OCTADIENE TERPOLYMERIZATION

| Ex | Catalyst | Al/Ti m/m | $P_{C2}$ atm | $P_{C3}$ atm | Diene mmoles | tp min | Activity $g_{pol}/g_{Ti}$ | $C_3$ % moles | Diene % moles | $r_E x r_P$ |
|---|---|---|---|---|---|---|---|---|---|---|
| 37 | $Ti(OCOCH_2CH_2CCl_3)_3$ (IX) | 224 | 4 | 1 | 60.7 | 30 | 22000 | 28.6 | 1.2 | 1.7 |

TABLE 5

CATALYTIC SYSTEMS BASED ON TITANIUM CHLOROCARBOXYLATES COPOLYMERIZATION OF ETHYLENE AND PROPYLENE IN LIQUID MONOMER

| Example | Catalyst | Yield g | Activity $g_{pol}/g_{Ti}$ | $C_3$ % moles | $M_w \times 10^{-3}$ | MWD |
|---|---|---|---|---|---|---|
| 38 Comp | $Ti(AcAc)_3$ (I) | 10.1 | 5000 | 25.5 | 385 | 30.3 |
| 39 | $Ti(OCOCCl_3)_3$ (IV) | 20.2 | 10000 | 30.1 | 431 | 9.2 |
| 40 | $TiCl(OCOCH_2CH_2CCl_3)_2$ (VIII) | 17.8 | 8800 | 28.4 | 110 | 4.1 |
| 41 | $Ti(OCOCH_2CH_2CCl_3)_3$ (IX) | 23.1 | 11500 | 29.7 | 173 | 3.8 |

Comments on the Tables

From the data of Tables 1 and 2, it can be seen how the catalysts of the present invention are capable of producing polymers with different propylene contents by varying the composition of the mixture of monomers fed. Under the same experimental conditions, the activities are always higher than the respective values indicated for the comparative examples (compare examples 19 with 22; 20 with 24 and 25; 29 with 32), the molecular weights (Mw) of the polymers vary from 100,000 to 1,000,000, whereas the MWD values are generally lower than the reference values (compare examples 19 with 22; 20 with 24 and 25; 21 with 26; 29 with 32). The polymers obtained show a % of incorporated $C_3$ which varies from about 30% to 70% in moles, whereas the value of the $r_E x r_P$ product is always less than 1 indicating a random incorporation of the comonomer contrary to what is observed in the comparative examples where it is always greater than 1, this showing a tendency to have blocks of the two monomers in the polymer.

From Table 3 it can be seen how the catalysts of the present invention are capable of producing EP(D)M terpolymers with a higher ENB content than that obtained in the comparative example and with the performances already indicated for the ethylene-propylene copolymers in terms of activity, Mw and MWD; Table 4 specifies the capacity of the catalysts of the present invention of incorporating dienes different from ENB, such as 7-methyl-1,6-octadiene.

Finally, the same considerations indicated for the data of Table 1 relating to the results obtained in solution can be applied to the data of Table 5, obtained operating in liquid monomer.

What is claimed is:

1. A titanium complex having general formula (I)

$$(RCOO)_n TiX_p \qquad (I)$$

wherein R is a monofunctional hydrocarbyl radical having from 1 to 20 carbon atoms and from 1 to 6 chlorine atoms;

X is selected from the group consisting of chlorine and bromine, p+n=2 or 3; and n is greater than or equal to 1.

2. The titanium complex according to claim 1, wherein X is chlorine.

3. The complex according to claim 1, wherein n+p=3.

4. The complex according to claim 1, wherein R—COO is

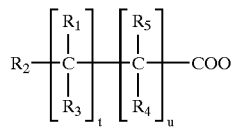

wherein $R_1$, $R_2$, $R_3$, $R_4$ and $R_5$, may be the same or different and are selected from the group consisting of Cl, a monofunctional hydrocarbyl radical, and a monofunctional hydrocarbon having at least one hydrogen atom substituted with chlorine, with the proviso that at least one of $R_1$ to $R_5$ is selected from the group consisting of chlorine and a mono-functional hydrocarbyl group containing chlorine; and t and u independently are from 0 to 10.

5. The complex according to claim 4, wherein t and u are independently from 0 to 5.

6. The complex according to claim 1, wherein R—COO is

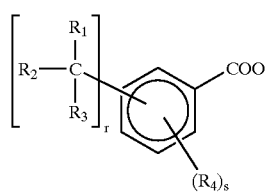

wherein:

$R_1$, $R_2$, $R_3$ and $R_4$ are selected from the group consisting of Cl, a monofunctional hydrocarbyl radical and a monofunctional hydrocarbon having at least one hydrogen atom substituted with chlorine, with the proviso that at least one of $R_1$ to $R_4$ is selected from the group consisting of chlorine and a monofunctional hydrocarbyl group containing chlorine; r and s are independently from 0 to 5, and r+s is from 1 to 5.

7. The complex according to claim 1, wherein R—COO is

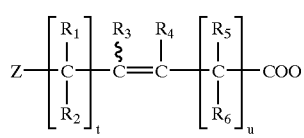

wherein:

$R_1$, $R_2$, $R_3$ and $R_4$ Z, $R_5$, and $R_6$ are selected from the group consisting of Cl, a monofunctional hydrocarbyl radical and a monofunctional hydrocarbon having at least one hydrogen atom substituted with chlorine, with the proviso that at least one of Z and $R_1$–$R_6$ is selected from the group consisting of chlorine and a monofunctional hydrocarbyl group containing chlorine;

t and u are independently from 0 to 10.

8. The complex according to claim 7, wherein t and u are independently from 0 to 5.

9. The complex according to claim 1, wherein R is a mono-functional hydrocarbyl radical selected from the group consisting of cycloalkyl, polycycloalkyl, cycloalkenyl, and polycycloalkenyl having from 3 to 20 C atoms, substituted with at least one chlorine, or with hydrocarbyl groups containing at least one chlorine.

10. The complex according to claim 1 selected from the group consisting of

Ti(OCOCCl$_3$)$_2$;

Ti(OCOCCl$_3$)$_3$;

TiCl(OCOCCl$_3$)$_2$;

TiCl$_2$(OCOCCl$_3$);

TiCl(OCOCH$_2$CH$_2$CCl$_3$)$_2$;

Ti(OCOCH$_2$CH$_2$CCl$_3$)$_3$;

Ti($_{2,4}$-Cl$_2$—C$_6$H$_3$—CH$_2$COO)$_3$;

Ti(CCl$_3$CH=CHCOO)$_3$;

Ti($_2$—Cl—C$_6$H$_{10}$COO)$_3$;

Ti(ClCH$_2$C$_6$H$_4$COO)$_3$;

Ti(C$_6$H$_5$CCl$_2$COO)$_3$; and

Ti[OCOCH(C$_6$H$_5$)CCl$_2$CH$_3$]$_3$.

11. A process for the preparation of the titanium complexes having general formula (I)

$$(RCOO)_n TiX_p \qquad (I)$$

wherein R is a monofunctional hydrocarbyl radical having from 1 to 20 carbon atoms and from 1 to 6 halogen atoms, selected from the group consisting of fluorine, chlorine and bromine;

X is selected from the group consisting of chlorine, bromine, and a beta-dicarbonyl group; or 2 X=O;

p+n=2, 3, 4 ; and n is greater than or equal to 1, which comprises:

(a) treatment of a thallium salt having the general formula RCOOTl, wherein R has the meaning defined above, with a titanium compound having the general formula TiY$_n$X$_s$, wherein (n+s=2, 3, 4); s≧1; X is selected from the group consisting of chlorine, bromine, and iodine, Y may be the same as or different from X, is a group of an anionic nature bound to Ti as anion in an ionic couple or with a covalent bond of the "σ" type; said treatment carried out in a hydrocarbyl solvent or in a chlorinated solvent;

(b) separation of a thallium halide formed in (a); and (c) isolation of the titanium complex having general formula (I).

12. A process for the preparation of the titanium complexes having general formula (I)

$$(RCOO)_n TiX_p \qquad (I)$$

wherein R is a monofunctional hydrocarbyl radical having from 1 to 20 carbon atoms and from 1 to 6 halogen atoms, selected from the group consisting of fluorine, chlorine and bromine, X is selected from the group consisting of chlorine, bromine, and a beta-dicarbonyl group; or 2 X=O;

p+n=2, 3, 4; and n is greater than or equal to 1, which comprises:

(a') direct reaction between a titanium compound having the general formula TiY$_n$X$_s$ with one or more carboxylic acids having the general formula RCOOH in an aliphatic or aromatic hydrocarbon solvent or in a chlorinated solvent, until the stoichiometric development of hydrochloric acid; and (b') isolation of the titanium complex having general formula (I) formed in (a').

13. A catalytic system for the co- and ter-polymerization of α-olefins comprising:

(a) a titanium complex having general formula (I), according to claim 1, (b) a reducing/chlorinating agent based on aluminum selected from the group consisting of formula (II) $AlR_nX_{3-n}$ (with n=1 or 2) and formula (III) $Al_2R_nX_{6-n}$ (n=1–5) wherein R is a $C_1$–$C_{20}$ alkyl group, X is chlorine or bromine; and (c) an organo-aluminum having general formula (IV) $AlR_3$ wherein R is a $C_1$–$C_{20}$ alkyl group.

14. The catalytic system according to claim 13, wherein X is chlorine.

15. A process for the preparation of the catalytic system according to claim 13, which comprises:

(i) contacting the reducing/chlorinating agent (b) with the titanium complex (a) dissolved in an aliphatic or aromatic hydrocarbon solvent, in the absence of the mixture of olefins to be polymerized and the aluminum trialkyl, for a time of from 1 minute to 30 minutes, at a temperature of from 0° C. to 50° C., with the formation of a catalytic pre-cursor; and ii) feeding the catalytic precursor obtained in (I) to the mixture of olefins to be co- or ter-polymerized containing the aluminum trialkyl (c).

16. A process for the preparation of EPR copolymers and EPDM terpolymers, comprising:

carrying out polymerization in the presence of the catalytic system according to claim 13.

17. The process according to claim 16, carried out in liquid phase at a pressure of from 15 to 50 atm. and at temperatures of from −5° C. to 75° C.

18. The process according to claim 17, wherein the temperature is from 25° C. to 60° C. and the pressure is from 6 to 35 atm.

19. The process according to claim 16, carried out in the presence of a catalytic system which comprises a titanium complex having the general formula $(CCl_3-(-CH_2-)_n-COO)_3Ti$, wherein n is from 0 to 2.

20. The complex according to claim 4, wherein t and u are independently from 0 to 5.

21. The complex according to claim 7, wherein t and u are independently from 0 to 5.

22. The process of claim 11, wherein X is chlorine.

23. The process of claim 15, wherein the contacting is carried out for a time of from 5 to 20 minutes and at a temperature of from 15 to 40° C.

24. The process according to claim 17, carried out in solution or suspension.

* * * * *